United States Patent
Martins et al.

(10) Patent No.: US 9,435,779 B2
(45) Date of Patent: *Sep. 6, 2016

(54) METHOD FOR QUANTITATION OF ACID SITES IN ACIDIC IONIC LIQUIDS USING SILANE AND BORANE COMPOUNDS

(71) Applicant: UOP LLC, Des Plaines, IL (US)

(72) Inventors: Susie Martins, Carol Stream, IL (US); Erin M. Broderick, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 269 days.

This patent is subject to a terminal disclaimer.

(21) Appl. No.: 14/270,033

(22) Filed: May 5, 2014

(65) Prior Publication Data

US 2015/0316519 A1 Nov. 5, 2015

(51) Int. Cl.
- G01N 31/10 (2006.01)
- G01N 31/22 (2006.01)
- B01J 31/02 (2006.01)

(52) U.S. Cl.
CPC ........... *G01N 31/22* (2013.01); *B01J 31/0284* (2013.01); *Y10T 436/153333* (2015.01)

(58) Field of Classification Search
CPC .............................. G01N 31/10; G01N 31/22
USPC .............................. 436/37, 61, 100–102, 163
See application file for complete search history.

(56) References Cited

U.S. PATENT DOCUMENTS

| | | | |
|---|---|---|---|
| 2,887,500 A | 5/1959 | McEntee | |
| 4,547,595 A | 10/1985 | Chang | |
| 4,824,657 A | 4/1989 | Jadhav | |
| 5,397,536 A * | 3/1995 | Nakano | G01N 31/224 422/422 |
| 7,285,698 B2 * | 10/2007 | Liu | C07C 2/58 585/709 |
| 7,651,970 B2 | 1/2010 | Elomari et al. | |
| 7,674,739 B2 | 3/2010 | Elomari et al. | |
| 7,674,740 B2 | 3/2010 | Harris et al. | |
| 7,678,727 B2 | 3/2010 | Harris et al. | |
| 7,691,771 B2 | 4/2010 | Harris et al. | |
| 7,727,925 B2 | 6/2010 | Elomari et al. | |
| 7,732,363 B2 | 6/2010 | Elomari et al. | |
| 7,732,364 B2 | 6/2010 | Chang et al. | |
| 7,737,067 B2 | 6/2010 | Elomari et al. | |
| 7,737,363 B2 | 6/2010 | Kambe | |
| 7,754,636 B2 | 7/2010 | Elomari et al. | |
| 7,825,055 B2 | 11/2010 | Elomari et al. | |
| 7,884,045 B2 | 2/2011 | Harris et al. | |
| 7,956,002 B2 | 6/2011 | Elomari et al. | |
| 7,995,495 B2 | 8/2011 | Lin | |
| 8,043,991 B2 * | 10/2011 | Ching | B01J 21/08 502/158 |
| 8,507,396 B2 | 8/2013 | Elomari et al. | |
| 8,524,623 B2 | 9/2013 | Timken et al. | |
| 8,658,426 B2 * | 2/2014 | Timken | B01J 31/0284 436/37 |
| 8,772,035 B2 * | 7/2014 | Timken | B01J 31/0284 436/37 |
| 2002/0016005 A1 * | 2/2002 | Campbell | G01N 21/41 436/100 |
| 2003/0186444 A1 * | 10/2003 | White | G01N 24/08 436/37 |
| 2004/0247898 A1 * | 12/2004 | Ogawa | C03C 17/009 428/447 |
| 2007/0142211 A1 | 6/2007 | Elomari et al. | |
| 2007/0142213 A1 | 6/2007 | Elomari et al. | |
| 2007/0142215 A1 | 6/2007 | Harris et al. | |
| 2007/0142216 A1 | 6/2007 | Harris et al. | |
| 2007/0142217 A1 | 6/2007 | Elomari et al. | |
| 2007/0142218 A1 | 6/2007 | Harris et al. | |
| 2007/0249485 A1 | 10/2007 | Elomari et al. | |
| 2007/0249486 A1 | 10/2007 | Elomari et al. | |
| 2009/0235574 A1 * | 9/2009 | Earle | B01J 31/0279 44/308 |
| 2009/0278085 A1 * | 11/2009 | Burkhardt | C07C 29/143 252/182.29 |
| 2010/0065476 A1 * | 3/2010 | Hommeltoft | C10G 29/205 208/108 |
| 2010/0093521 A1 * | 4/2010 | Ching | B01J 21/08 502/158 |
| 2010/0129921 A1 * | 5/2010 | Timken | B01J 31/0284 436/96 |
| 2010/0130804 A1 | 5/2010 | Timken et al. | |
| 2010/0147740 A1 | 6/2010 | Elomari et al. | |
| 2010/0297532 A1 * | 11/2010 | Beste | C07D 233/54 429/498 |
| 2011/0111508 A1 * | 5/2011 | Timken | B01J 31/0284 436/37 |
| 2011/0183423 A1 * | 7/2011 | Timken | B01J 31/0284 436/37 |
| 2011/0184219 A1 * | 7/2011 | Timken | B01J 31/0284 585/727 |
| 2011/0294172 A1 * | 12/2011 | Lozano | C12P 7/649 435/131 |
| 2012/0283500 A1 | 11/2012 | Liu et al. | |
| 2015/0316518 A1 * | 11/2015 | Martins | G01N 31/10 436/37 |

FOREIGN PATENT DOCUMENTS

CN 102666444 A 9/2012
JP 55001870 1/1980

OTHER PUBLICATIONS

Childs, R. F. et al, Canadian Journal of Chemistry 1982, 60, 801-808.*
Piao, L. Y. et al, Catalysis Today 2004, 93-95, 301-305.*
Chen, Y. et al, Molecules 2010, 15, 9486-9495.*

(Continued)

*Primary Examiner* — Arlen Soderquist

(57) ABSTRACT

A method of quantifying an amount of Brønsted acid sites in an acidic ionic liquid is described. The method involves adding a known amount of at least one silane or borane compound to the acidic ionic liquid being analyzed. The Brønsted acid sites in the acidic ionic liquid react with the silane or borane compound to form a silyl or boryl compound, resulting in an ionic liquid phase and a hydrocarbon phase which contains the silyl or boryl compound. The amount of silyl or boryl compound in the hydrocarbon phase is measured. From the measured amount of silyl or boryl compound formed, the amount of Brønsted acid sites can be determined.

20 Claims, 2 Drawing Sheets

(56) References Cited

OTHER PUBLICATIONS

Jiang, Y. et al, Industrial & Engineering Chemistry Research 2011, 50, 1893-1898.*

Schmidt et al., "Disproportionation of Light Paraffins," Energy & Fuels (2008), vol. 22, 1812-1823.

Iranpoor et al. "Diphenylphosphinite ionic liquid (IL-OPPh2): A solvent and ligand for palladium . . ."Journal of Organometallic Chemistry(2010), 695(6), 887-890.

Gevorgyan et al. "Reduction of Alkoxysilanes, Halo-silanes and -Germanes with Lithium . . . " Journal of Organometallic Chemistry (1985), vol. 284, C31-C32.

* cited by examiner

METHOD FOR QUANTITATION OF ACID SITES IN ACIDIC IONIC LIQUIDS USING SILANE AND BORANE COMPOUNDS

BACKGROUND OF THE INVENTION

Commercially, the alkylation of isoparaffins is catalyzed by acids such as sulfuric acid and hydrofluoric acid. Conjunct polymer (acid soluble oils, (ASO) also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

There has been a move to replace the use of sulfuric acid and hydrofluoric acid with more environmentally friendly materials.

One such process utilizes acidic ionic liquids as catalysts in hydrocarbon conversion processes, such as alkylation, isomerization, disproportionation, and oligomerization. Conjunct polymers are byproducts of the hydrocarbon reaction using ionic liquids, and they form a complex with the ionic liquid catalyst. The ionic liquid catalyst loses its effectiveness over time as the amount of conjunct polymer increases. It must then either be replaced or regenerated. Because ionic liquids are typically fairly expensive, processes for regenerating the ionic liquid catalysts are needed.

A variety of methods for regenerating ionic liquids have been developed. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the CP to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [1-butylpyridinium][Cl] would be added to the ionic liquid (e.g. [1-butylpyridinium][$Al_2Cl_7$]) containing the conjunct polymer followed by an inert hydrocarbon. After a given time of mixing, the hydrocarbon layer would be separated, resulting in a regenerated ionic liquid. The solid residue would be converted to ionic liquid by adding $AlCl_3$. See e.g., U.S. Pat. No. 7,737,363 and U.S. Pat. No. 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

With the increasing use of regenerated ionic liquids, it is important to determine the effectiveness of the regenerated ionic liquid. Quantifying the Brønsted acid sites in these systems is quite challenging. US 2010/0129921 teaches the use of titrating hydrolyzed ionic liquid samples with a basic reagent to calculate the acid content in the sample. However, this method is destructive, and the ionic liquid is rendered unusable in the process.

Moreover, direct contact of the spent ionic liquid with basic reagents, such as amines, almost always results in the formation of an amine-$AlCl_3$ complex. This deactivates the ionic liquid. Furthermore, it provides little information about the Brønsted sites because the amine has higher affinity for the Lewis acid sites.

Therefore, there remains a need for methods of quantifying the acidity of ionic liquids.

SUMMARY OF THE INVENTION

One aspect of the invention involves a method of quantifying an amount of Brønsted acid sites in an acidic ionic liquid. In one embodiment, the method includes contacting a known amount of at least one silane or borane compound with the acidic ionic liquid, the Brønsted acid sites in the acidic ionic liquid reacting with the at least one silane or borane compound resulting in an ionic liquid phase and a hydrocarbon phase comprising at least one silyl or boryl compound; measuring an amount of the at least one silyl or boryl compound in the hydrocarbon phase; and determining the amount of Brønsted acid sites from the measured amount of the at least one silyl or boryl compound.

DETAILED DESCRIPTION OF THE INVENTION

Figure 1:
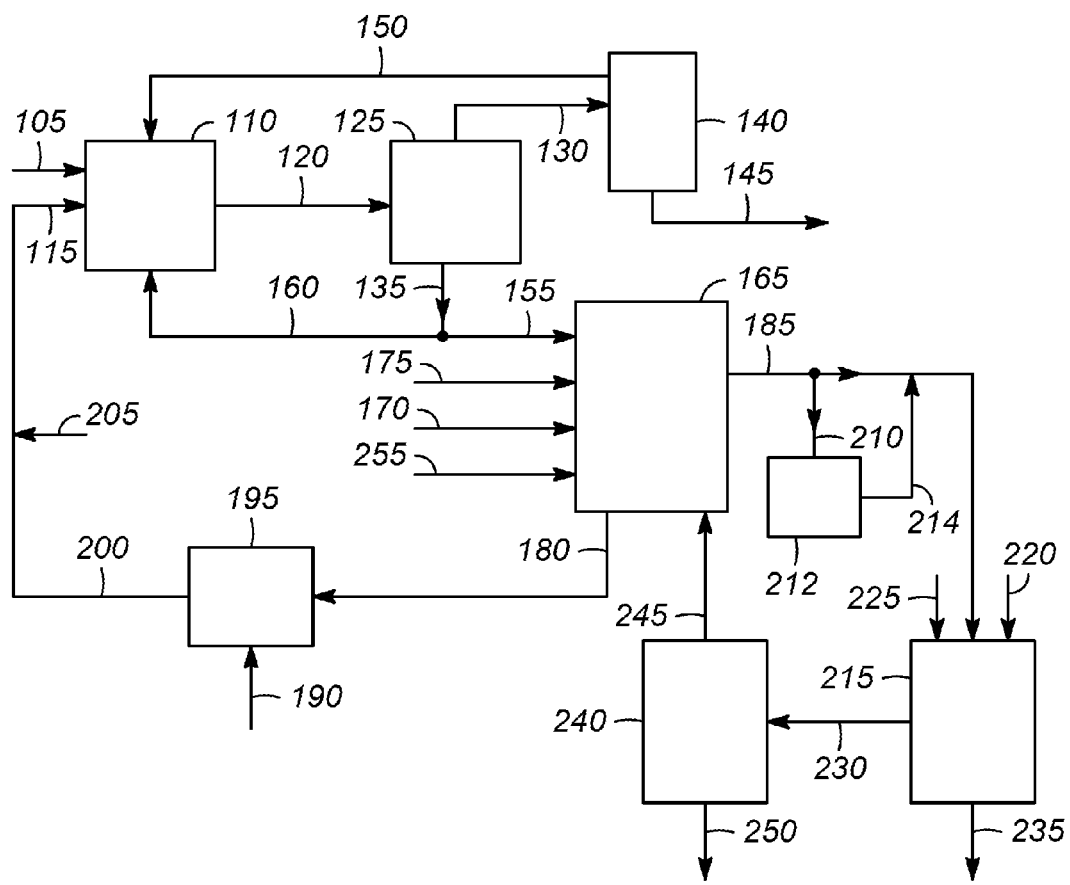
FIG. 1 illustrates one embodiment of an alkylation process using the quantitation method according to the present invention.

The use of silane and borane compounds as efficient regenerants in the removal of conjunct polymer from ionic liquids has been described in U.S. application Ser. No. 14/269,943, now U.S. Pat. No. 9,120,092 entitled Regeneration of an Acidic Catalyst by Silane Addition, filed on even date herewith, U.S. application Ser. No. 14/270,008, now U.S. Pat. No. 9,096,618 entitled Regeneration of Spent Silane Compound, filed on even date herewith, which are incorporated herein by reference, U.S. application Ser. No. 14/269,978 now U.S. Pat. No. 9,221,043 entitled Regeneration of an Acidic Catalyst by Borane Addition, filed on even date herewith. In this mechanism, the acid sites associated with the conjunct polymer react with the silane or borane compound to produce a silyl or boryl compound and liberate the conjunct polymer into the hydrocarbon phase because it is no longer charged. The silyl or boryl compound can then be regenerated to the silane or borane compound and reused.

An analogous mechanism can be used to quantify the number of Brønsted acid sites in an ionic liquid, whether fresh or spent. The method can be useful in controlling the particular acid level of the ionic liquid in a continuous process, such as alkylation, oligomerization, isomerization, disproportionation, reverse disproportionation, and the like. It can also be useful in ensuring that fresh ionic liquid or regenerated ionic liquid contains the appropriate acid level before being fed to a reaction zone. The method is non-destructive, so there is no loss of ionic liquid and the ionic liquid tested can be used in the process. Moreover, the titrating agent does not react with the $AlCl_3$ Lewis acid sites in the ionic liquid.

The method involves adding a known amount of at least one silane or borane compound to the acidic ionic liquid being analyzed. The Brønsted acid sites in the acidic ionic liquid react with the silane or borane compound to form a silyl or boryl compound, resulting in an ionic liquid phase and a hydrocarbon phase which contains the silyl or boryl compound. The amount of silyl or boryl compound in the hydrocarbon phase is measured. The amount of silyl or boryl compound can be measured using any suitable method, including, but not limited to, gas chromatography, infrared spectroscopy, nuclear magnetic resonance spectroscopy, x-ray fluorescence, liquid chromatography, ion chromatography, or combinations thereof.

From the measured amount of silyl or boryl compound formed, the amount of Brønsted acid sites can be determined. Analysis of the hydrocarbon phase using gas chromatography provides percent conversion on a weight basis. The percent conversion of silyl or boryl compound as measured is used to calculate the number of moles of silyl or boryl compound converted based on how much was loaded normalized by the weight of the ionic liquid. When the hydrocarbon phase is analyzed by infrared spectroscopy, the amount of silyl and boryl compound can be determined after calibration with various standards of known concentrations. Nuclear magnetic resonance spectroscopy can be performed on the organic phase and provides a percent conversion of the silane or borane compound to the silyl or boryl compound on a molar basis. The number of moles of silyl or boryl compound detected is related to the number of acid sites in the ionic liquid.

The quantitation method can be used for both fresh ionic liquid and spent ionic liquid. It can be used in a hydrocarbon conversion process for quality control of the ionic liquid.

The method can be used to control the acid level in the ionic liquid in a continuous process. It could also be used to ensure that a newly synthesized ionic liquid or regenerated ionic liquid contains an appropriate acid level before it is introduced into the process reactor.

In embodiments where the ionic liquid has been used in a hydrocarbon conversion process and conjunct polymer is present, the method can be used to determine the amount of fresh acid sites. The percent of silane or borane converted is measured, along with the weight percent of conjunct polymer associated with any spent acid sites. The amount of conjunct polymer can be subtracted from the total percent of silane or borane converted, and the number of fresh acid sites can then be determined.

The ionic liquid and the silane compound are contacted for a period of time sufficient to allow the Brønsted acid sites in the ionic liquid to react with the silane or borane compound. For silane compounds, this will typically take in the range of about 5 sec to about 1 hr, or about 1 min to about 45 min, or about 1 min to about 30 min, or about 1 min to about 15 min. For borane compounds at room temperature, the reaction is slower than the silane reaction, e.g., many hours. The time is less at elevated temperatures, e.g., less than 2 hr at 50° C. By the term about, we mean within 10% of the specified value, or within 5%, or within 1%.

The ionic liquid, the solvent, and the silane or borane compound are typically mixed while being contacted.

The contacting typically takes place at a temperature in the range of from about −20° C. to the decomposition temperature of the ionic liquid. A typical temperature range is about 20° C. to about 80° C. In some embodiments, the contacting with silane compounds takes place at room temperature. In some embodiments with borane compounds, the contacting takes place at temperatures in the range of about 40° C. to about 80° C., or about 70° C.

The pressure is typically ambient pressure, although higher or lower pressures could be used if desired.

In some embodiments, the reaction is conducted under an inert gas so that hydrolysis of the silane or borane does not occur. In some embodiments, the ionic liquid may also hydrolyze, so these reactions are desirably conducted under an inert gas. Suitable inert gases include, but are not limited to, nitrogen, helium, neon, argon, krypton, and xenon.

In some embodiments, a solvent and a silane or borane compound are added to the ionic liquid. The solvent and the silane or borane compound can be pre-mixed and added together, or they can be added separately, either at the same time or sequentially. Solvent is not always necessary, but it will maximize recovery, removal, and separation of the conjunct polymer. When the silane or borane compound is mixed with a solvent for the contacting step, the solvent can be recovered before or after separating the conjunct polymer from the spent silane or borane. The recovered solvent can be recycled and reused in the process.

In some embodiments, the volume ratio of the solvent to the ionic liquid is in a range of about 0.25:1 to about 10:1.

In some embodiments where conjunct polymer is present, the molar ratio of the silane compound to the conjunct polymer is in a range of about 1:1 to about 5:1, or about 2:1 to about 3:1. In some embodiments where conjunct polymer is present, the molar ratio of the borane compound to the conjunct polymer is in a range of about 0.5:1 to about 5:1, or about 2:1 to about 3:1. In some embodiments, the silane or borane compound can be present in excess of the amount needed for reaction with the conjunct polymer, and the excess silane or borane compound can act as a solvent. In these cases, the molar ratio of the silane or borane compound to the conjunct polymer is more than 5:1, e.g., in the range of 10:1 to about 1000:1.

The contacting can take place in any suitable process, such as solvent extraction, or contacting in one or more mixer/settlers.

The reaction will proceed simply by contacting the silane or borane compound with the acidic ionic liquid catalyst. However, the mixture can be stirred to increase the contact between the silane or borane compound and the acidic catalyst.

The contacting step may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants.

The ionic liquid phase is generally separated from the hydrocarbon phase containing the silyl or boryl compound before the amount of silyl or boryl compound is measured. In a system without stirring or after stirring is ended, the components can separate into two phases based on the density difference between the ionic liquid phase and the hydrocarbon phase. The ionic liquid will settle to the bottom, and the hydrocarbon phase containing the silyl or boryl compound will be on top of the ionic liquid layer. Increasing the volume of the top layer with additional solvent will increase conjunct polymer recovery. Separation typically takes on the order of a few minutes to hours; it is generally less than about 1 hr.

After the silyl or boryl compound has been measured, the portion of the hydrocarbon phase that was measured can be returned to the overall hydrocarbon stream and processed with that stream to regenerate the silane or borane compound from the silyl or boryl compound.

The silyl or boryl compound can be chemically reduced to regenerate the silane or borane compound. One method of regeneration is reaction with one or more compounds containing hydrogen, such as one or more metal hydrides. The reaction can take place in a suitable solvent, such as tetrahydrofuran (THF), or toluene. The silyl or boryl compound is converted back to the silane or borane compound and a metal salt byproduct. Suitable metal hydrides include, but are not limited to, LiH, NaH, $CaH_2$, $NaAlH_4$, $LiAlH_4$, KH, $NaBH_4$, diisobutylaluminum hydride, and the like.

The silane or borane regeneration reaction can take place in a few hours at temperatures in the range of about 25° C. to about 70° C., depending on the metal hydride and solvent used.

In some embodiments where conjunct polymer is present, the separation of the conjunct polymer from the silyl or boryl compound may not be complete because the silyl or boryl compound may co-boil with the lower molecular weight conjunct polymer making complete removal difficult.

In some embodiments where conjunct polymer is present, after removing the conjunct polymer from the ionic liquid, the ionic liquid can be reactivated by the addition of an acid or an acid precursor. Suitable acids and acid precursors include, but are not limited to, HCl, tert-butyl chloride, or 2-chlorobutane. The acid precursor can be any molecule that will break down to form the acid. Reactivation of the ionic liquid with acid or acid precursor typically takes about 5 sec to about 30 min. It can be done at a range of temperatures. For convenience, it is typically done at the same conditions as the hydrocarbon conversion process which generates the conjunct polymer.

Rather than using a solvent extraction process, the acidic ionic liquid can be passed through a resin containing silane or borane moieties. Suitable resins include, but are not limited to, polystyrene and polyester. The silane and borane moieties react with the acid sites.

The ionic liquid containing the conjunct polymer can be pre-treated before it is contacted with the silane compound. The pretreatment can be used to remove any free acid, such as HCl, which might increase the consumption of the silane or borane compound, and/or any dissolved solvent, which might associate with the conjunct polymer. The pretreatment can be in a fractionation column, for example.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

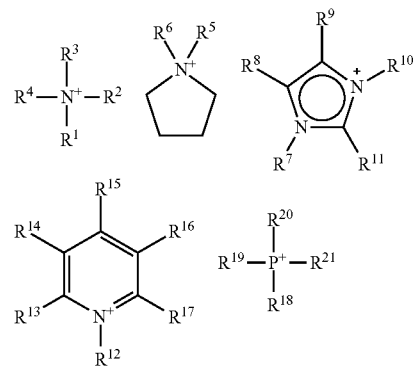

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The silane compound can be any compound with a reactive Si—H moiety. In some embodiments, the silane compound is an organosilane. There can be one or more silanes. Suitable silane compounds include, but are not limited to, silanes having the formulas: $R_3SiH$, $R_2SiH_2$, $RSiH_3$, or $SiH_4$ where each R is independently selected from hydrocarbons or halides. Examples of suitable silanes include triethylsilane, trimethylsilane, triisopropylsilane, and the like. In some embodiments, the silane can be a silane-containing resin.

The silyl compound will be the reaction product of the silane compound and the acid site on the ionic liquid and the conjunct polymer, if present. When the silane has one the formulas above, the silyl compound will have the formula: $R_3SiX$, $R_2SiX_2$, $RSiX_3$, or $SiX_4$, where each R is independently selected from hydrocarbons, and each X is independently selected from halides.

The borane compound can be any borane compound having a reactive B—H bond. In some embodiments, the borane compound is an organoborane. There can be one or more boranes. Suitable borane compounds include, but are not limited to, boranes having the formulas: $R_2BH$ or where each R is independently selected from hydrocarbons or halides, or $B_2H_6$, or combinations thereof. Examples of suitable boranes include 9-borabicyclo(3,3,1)nonane, trimesitylborane, trisec-butylborane, and diborane and the like. In some embodiments, the borane can be a borane-containing resin.

The boryl compound will be the reaction product of the borane product and the acid site on the ionic liquid and the conjunct polymer, if present.

The solvent for use with the silane or borane will depend on the acidic catalyst being regenerated. The solvent can be any solvent which is capable of forming a separate phase from the catalyst phase. There can be one or more solvents. Suitable solvents for halometallate ionic liquids include, but are not limited to, $C_4$ to $C_{10}$ paraffins, including n-paraffins, isoparaffins, cyclic paraffins, and aromatic solvents. If the ionic liquid is soluble in hydrocarbons, more polar solvents which are not miscible in the ionic liquid would be used.

In order to explain the method, it will be described in the context of a hydrocarbon conversion process using a silane compound. As will be understood by those of skill in the art, the method is not limited to use in hydrocarbon conversion processes; it can be used anywhere where quantifying the amount of Brønsted acid in an acidic ionic liquid is needed.

FIG. 1 illustrates one embodiment of a hydrocarbon conversion process 100, such as alkylation, oligomerization, isomerization, disproportionation, reverse disproportionation, and the like. For ease of discussion, the process will be described for use in an alkylation process using tributylhexylphosphonium chloroaluminate ionic liquid (TBHP—$Al_2Cl_7$), triethylsilane (TESi—H), and n-butane ($nC_4$) solvent. Other acidic catalysts, (including other acidic ionic liquids), silane and borane compounds, and solvents could also be used, as would be understood by those skilled in the art.

The hydrocarbon feed 105 containing butanes and butenes is sent to alkylation reaction zone 110. An ionic liquid catalyst stream 115 is also introduced into the alkylation reaction zone 110. The butenes are alkylated in the alkylation reaction zone 110 resulting in a hydrocarbon phase containing the alkylated product and an ionic liquid phase. Over time, the ionic liquid phase will contain conjunct polymer as a result of the alkylation process. As the amount of conjunct polymer increases, the ionic liquid becomes deactivated.

The reaction mixture 120 from the alkylation reaction zone 110 is sent to a separation zone 125 where the hydrocarbon phase 130 is separated from the ionic liquid phase 135. The separation can occur based on the density difference between the hydrocarbon phase 130 and the ionic liquid phase 135.

The hydrocarbon phase 130 is sent to a separation zone 140 where it is separated into at least an alkylate product stream 145 and an isobutane stream 150. The alkylate stream is recovered and used in a gasoline product, for example. The isobutane stream 150 can be recycled to the alkylation reaction zone 110.

At least a portion 155 of the ionic liquid phase 135 is sent to the reactive extraction zone 165. In some embodiments, all of the ionic liquid phase 135 is sent to the reactive extraction zone 165. In some embodiments, a portion 160 of the ionic liquid phase 135 from the separation zone 125 is recycled to the alkylation reaction zone 110.

The portion 155 of the ionic liquid phase 135 is introduced into the reactive extraction zone 165. The ionic liquid is TBHP—$Al_2Cl_7$. The portion 155 of the ionic liquid phase 135 which contains conjunct polymer contains

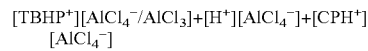
$[TBHP^+][AlCl_4^-/AlCl_3]+[H^+][AlCl_4^-]+[CPH^+][AlCl_4^-]$ where $[CPH^+]$ represents the protonated conjunct polymer.

A known amount of silane compound 170 is introduced into the reactive extraction zone 165. In some embodiments, a solvent stream 175 is also introduced into the reactive extraction zone 165. If present, the solvent stream 175 can be introduced separately, or mixed with the silane compound 170 prior to being introduced.

The silane compound 170 and the solvent stream 175 contain

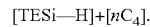
$[TESi—H]+[nC_4]$.

The portion 155 of the ionic liquid phase 135 containing the conjunct polymer reacts with the TESi—H to form triethylsilylchloride (TESi—Cl). Although not wishing to be bound by theory, it is believed that a reaction occurs between the TESi—H and the acid sites associated with the conjunct polymers. When the conjunct polymer is no longer protonated, it becomes an organic-like molecule (no longer charged), so it is easily transferred to the organic phase.

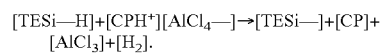
$[TESi—H]+[CPH^+][AlCl_4—]\rightarrow[TESi—]+[CP]+[AlCl_3]+[H_2]$.

The ionic liquid phase with the conjunct polymer removed 180 can be separated from the hydrocarbon phase 185 by taking advantage of the fact that it has a higher density than the hydrocarbon phase 185.

The ionic liquid phase 180 contains dissolved/suspended $AlCl_3$, which is reactivated by adding an acid 190, such as HCl, in zone 195 to restore the active acid site:

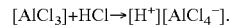
$[AlCl_3]+HCl\rightarrow[H^+][AlCl_4^-]$.

The re-activated ionic liquid 200 contains

$[TBHP^+][AlCl_4^-/AlCl_3]+[H^+][AlCl_4^-]$.

Fresh ionic liquid 205 can be added to the reactivated ionic liquid 200, if needed, and the re-activated ionic liquid 200 can be recycled back to the alkylation reaction zone 110 as ionic liquid catalyst stream 115.

The hydrocarbon phase 185 contains the TESi—, solvent, conjunct polymer, hydrogen, and any unreacted TESi—H.

$[TESi—]+[nC_4]+[CP]+[H_2]+[TESi—H]$.

A portion 210 of the hydrocarbon phase 185 is analyzed in an analysis zone 212 to measure the amount of the silyl compound, TESi—, by gas chromatography, for example.

The amount of Brønsted acid sites can be determined from the measured amount of silyl compound.

In some embodiments, conjunct polymer can be detected and quantified by gas chromatography analysis while simultaneously detecting the silyl (or boryl) compound.

If conjunct polymer is present (however determined), the amount of fresh and spent acid sites can be decoupled by subtracting the number of sites associated with the conjunct polymer from the total number of acid sites to determine the number of fresh sites.

The analysis of the portion 210 of the hydrocarbon phase 185 can be done continuously or intermittently, as desired.

Because the analysis is not destructive, stream 214 can be combined with the hydrocarbon stream 185 for treatment.

The TESi— in the hydrocarbon phase 185 is reacted to regenerate the TESi—H in a reaction zone 215. One method of regenerating the TESi— is with reducing agents that contain H$^-$, such as metal hydrides. The metal hydride 220 is added to reaction zone 215. A second solvent 225 is also added.

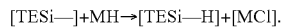

[TESi—]+MH→[TESi—H]+[MCl].

The metal salt 235 is removed from reaction zone 215. The effluent 230 from the reaction zone 215 contains the regenerated TESi—H, the solvent, and the conjunct polymer.

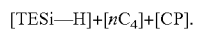

[TESi—H]+[nC$_4$]+[CP].

The effluent 230 from the reaction zone 215 can be sent to a separation zone 240 where the solvent and TESi—H 245 are separated from the conjunct polymer 250. The solvent and TESi—H stream 245 from separation zone 240 can be recycled to the reactive extraction zone 165. The second solvent goes through the process and is recycled with the TESi—H to the reactive extraction zone 165 in stream 245.

Fresh ionic liquid 255 can also be sent to the reaction extraction zone 165 for analysis and determination of the amount of Brønsted acid sites. In this case, there is no conjunct polymer present.

Example 1

A series of experiments were run in which 4 g of fresh tributylhexylphosphonium heptachloroaluminate ionic liquid, and samples of spent ionic liquid containing varying amounts of conjunct polymer were mixed with TESi—H (see Table 1). The amount of TESi—H ranged from 0.24 g to 1.2 g.

The spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a stirred 300 mL autoclave stirred at 1200 rpm. The mixture was continuously transferred to a gravity separator and the ionic liquid recycled to the alkylation reactor. Flow rates and feed ratios varied over the course of the reaction which took place over several days to weeks for the various samples. At the end of each run, the heavy fraction containing ionic liquid was collected and stored under nitrogen. The % conjunct polymer in each of the spent samples was determined by extraction and isolation of conjunct polymer. A known mass of the spent ionic liquid was mixed with water. The conjunct polymer was extracted from the ionic liquid/water mixture with hexane. The hexane was removed on a rotary evaporator and the mass of the isolated conjunct polymer was determined.

The amount of silyl compound produced was measured using a gas chromatograph. The measured amount of silyl compound produced was converted to moles and normalized by the weight of the ionic liquid.

Additional experiments were run in which a known amount of 2-chlorobutane (HCl precursor) was added, and the same test was run.

Figure 2:
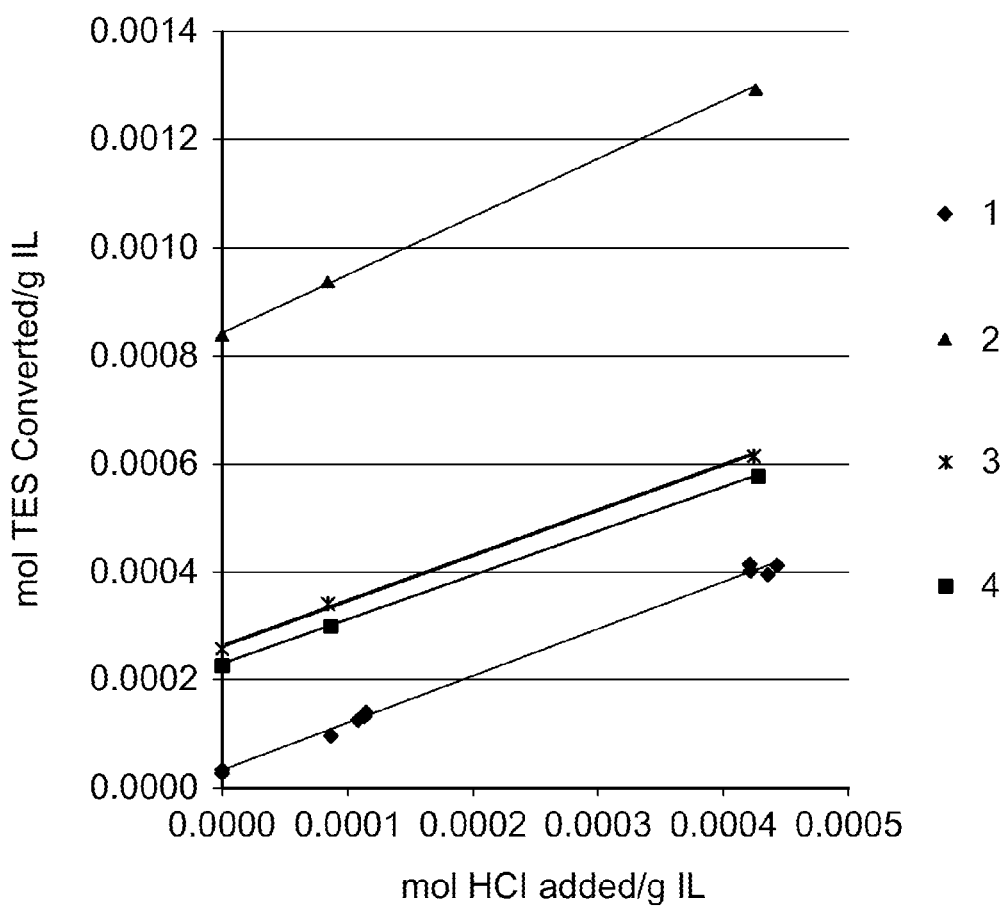
FIG. 2 is a graph showing the moles of a silane compound converted as a function of the mol of an acid added normalized by the weight of the ionic liquid.

The results are shown in FIG. 2. The x-axis is the amount of HCl added (as 2-chlorobutane) normalized by the weight of the ionic liquid. The y-intercept is the amount of acid sites in the ionic liquid (prior to dosing). In the case of fresh IL, these represent active acid sites and the case of spent IL, these represent the cumulative amount of acid sites, fresh and spent sites (associated with the conjunct polymer). There is a very good correlation between the amount of TESi— converted as a function of acid present.

TABLE 1

| Sample No. | Composition - wt % CP |
|---|---|
| 1 | 0% |
| 2 | 10.42% |
| 3 | 6.16% |
| 4 | 3.04% |

Example 2

A series of experiments were run in which 1 g of fresh tributylhexylphosphonium heptachloroaluminate ionic liquid were mixed with 0.4M solution of 9-borabicyclo(3,3,1) nonane (9-BBN) in hexane. 1 ml of the 9-BBN solution was added to each ionic liquid sample. A known amount (10 mg to 30 mg) of 2-chlorobutane was added.

The amount of converted boryl compound was measured using NMR spectroscopy of the organic hexane layer. The measured amount of converted boryl compound was converted to moles and normalized by the weight of the ionic liquid.

Figure 3:
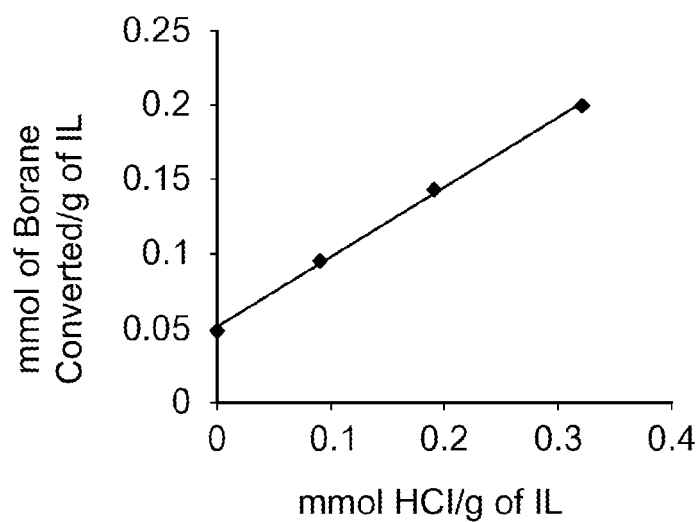
FIG. 3 is a graph showing the moles of a borane compound converted as a function of the mol of an acid added normalized by the weight of the ionic liquid.

The results are shown in Table 2 and FIG. 3. The x-axis is the amount of HCl added (as 2-chlorobutane) normalized by the weight of the ionic liquid. The y-intercept relates to the amount of acid sites in the ionic liquid (prior to dosing). These represent active acid sites.

TABLE 2

| mmol HCl added/g IL | mmol borane converted/g IL |
|---|---|
| 0 | 0.048 |
| 0.09 | 0.096 |
| 0.19 | 0.144 |
| 0.32 | 0.2 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method of quantifying an amount of Brønsted acid sites in an acidic ionic liquid comprising:
contacting a known amount of at least one silane or borane compound with the acidic ionic liquid, the Brønsted acid sites in the acidic ionic liquid reacting with the at least one silane or borane compound resulting in an ionic liquid phase and a hydrocarbon phase comprising at least one silyl or boryl compound;
measuring an amount of the at least one silyl or boryl compound in the hydrocarbon phase;
determining the amount of Brønsted acid sites from the measured amount of the at least one silyl or boryl compound.

2. The method of claim 1 wherein measuring the amount of the at least one silyl or boryl compound comprises measuring the amount of the at least one silyl or boryl compound using gas chromatography, infrared spectroscopy, nuclear magnetic resonance spectroscopy, x-ray fluorescence, liquid chromatography, ion chromatography, or combinations thereof.

3. The method of claim 1 further comprising separating the ionic liquid phase from the hydrocarbon phase before measuring the amount of the at least one silyl or boryl compound.

4. The method of claim 3 further comprising adding an acid or acid precursor to the ionic liquid phase to regenerate the Brønsted acid sites in the acidic ionic liquid.

5. The method of claim 3 further comprising chemically reducing the at least one silyl or boryl compound with a compound containing hydrogen to regenerate the at least one silane or borane compound.

6. The method of claim 5 wherein the compound containing hydrogen comprises a metal hydride.

7. The method of claim 6 wherein the metal hydride comprises LiH, NaH, $CaH_2$, $NaAlH_4$, $LiAlH_4$, KH, $NaBH_4$, diisobutylaluminum hydride, or combinations thereof.

8. The method of claim 1 wherein the at least one silane compound has the formula: $R_3SiH$, $R_2SiH_2$, $RSiH_3$, or $SiH_4$, where each R is independently selected from hydrocarbons or halides.

9. The method of claim 1 wherein the at least one borane compound comprises a compound having a formula $R_2BH$, where each R is independently selected from hydrocarbons or halides, or $B_2H_6$, or combinations thereof.

10. The method of claim 9 wherein the hydrocarbon solvent comprises a paraffin having up to 10 carbon atoms, an aromatic, or the at least one silane or borane compound.

11. The method of claim 1 wherein contacting the known amount of the at least one silane or borane compound with the acidic ionic liquid comprises contacting the known amount of the at least one silane or borane compound with the acidic ionic liquid in a hydrocarbon solvent.

12. The method of claim 1 wherein the acidic ionic liquid further comprises a conjunct polymer, the conjunct polymer reacting with the at least one silane or borane compound, and further comprising:
determining an amount of conjunct polymer from the measured amount of the at least one silyl or boryl compound.

13. The method of claim 12 wherein the conjunct polymer reacting with the at least one silane or borane compound releases conjunct polymer and additional silyl or boryl compound, the hydrocarbon phase further comprising the conjunct polymer and the additional silyl or boryl compound, and further comprising separating the conjunct polymer from the hydrocarbon phase.

14. The method of claim 1 wherein contacting the known amount of the at least one silane or borane compound with the acidic ionic liquid further comprises mixing the known amount of the at least one silane or borane compound with the acidic ionic liquid.

15. A method of quantifying an amount of Brønsted acid sites in an acidic ionic liquid comprising:
contacting a known amount of at least one silane or borane compound with the acidic ionic liquid, the Brønsted acid sites in the acidic ionic liquid reacting with the at least one silane or borane compound resulting in an ionic liquid phase and a hydrocarbon phase comprising at least one silyl or boryl compound;
separating the ionic liquid phase from the hydrocarbon phase;
measuring an amount of the at least one silyl or boryl compound in the hydrocarbon phase using gas chromatography, infrared spectroscopy, nuclear magnetic resonance spectroscopy, x-ray fluorescence, liquid chromatography, ion chromatography, or combinations thereof;
determining the amount of Brønsted acid sites from the measured amount of the at least one silyl or boryl compound.

16. The method of claim 15 further comprising chemically reducing the at least one silyl or boryl compound with a compound containing hydrogen to regenerate the at least one silane or borane compound.

17. The method of claim 16 wherein the compound containing hydrogen comprises a metal hydride.

18. The method of claim 15 wherein the at least one silane compound has the formula: $R_3SiH$, $R_2SiH_2$, $RSiH_3$, or $SiH_4$, where each R is independently selected from hydrocarbons or halides.

19. The method of claim 15 wherein the at least one borane compound comprises a compound having a formula $R_2BH$, where each R is independently selected from hydrocarbons or halides, or $B_2H_6$, or combinations thereof.

20. The method of claim 15 wherein contacting the known amount of the at least one silane or borane compound with the acidic ionic liquid comprises contacting the known amount of the at least one silane or borane compound with the acidic ionic liquid in a hydrocarbon solvent.

* * * * *